United States Patent [19]

Katner

[11] 3,962,272

[45] June 8, 1976

[54] 1H-TETRAZOLE-1-ACETATE ESTERS AND ACIDS AND PROCESS THEREFOR

[75] Inventor: Allen S. Katner, Indianapolis, Ind.

[73] Assignee: Eli Lilly and Company, Indianapolis, Ind.

[22] Filed: Aug. 5, 1974

[21] Appl. No.: 494,599

Related U.S. Application Data

[63] Continuation-in-part of Ser. No. 280,625, Aug. 14, 1972, abandoned.

[52] U.S. Cl. .................................... 260/308 D
[51] Int. Cl.² ................................ C07D 257/04
[58] Field of Search ......................... 260/308 D

[56] References Cited
UNITED STATES PATENTS

| | | | |
|---|---|---|---|
| 3,073,731 | 1/1963 | Cohen et al. | 149/92 |
| 3,468,874 | 9/1969 | Raap et al. | 260/239.1 |
| 3,767,667 | 10/1973 | Kamiya et al. | 260/308 D |

*Primary Examiner*—Frederick E. Waddell
*Attorney, Agent, or Firm*—William C. Martens, Jr.; Everet F. Smith

[57] ABSTRACT

Novel 1H-tetrazole-1-acetate esters and acids are prepared by reacting azidoacetate esters and acids with certain acyl cyanides or cyanoformates. The products of the process are useful as intermediates in the preparation of 1H-tetrazole-1-acetic acids which have utility in preparing certain cephalosporin and penicillin antibiotics.

11 Claims, No Drawings

1H-TETRAZOLE-1-ACETATE ESTERS AND ACIDS AND PROCESS THEREFOR

CROSS REFERENCE

This is a continuation-in-part of application Ser. No. 280,625, filed Aug. 14, 1972, now abandoned.

BACKGROUND OF THE INVENTION a. Tetrazoleacetic acid Chemistry

In the *Journal of Organic Chemistry*, Vol. 21, (1956), pages 311–315, in an article entitled "Studies in Tetrazole Chemistry, IV, Tetrazoleacetic Acids and Esters", C. R. Jacobson et al. describe a method for preparing 5-substituted-1-tetrazole-1-acetic esters by reacting an ester of an N-acylated α-amino acid sequentially with phosphorus pentachloride and hydrazoic acid.

In the *Journal of Organic Chemistry*, Vol 22, (1957), pages 933–936, in an article entitled "Synthesis of 1-Substituted Tetrazoles" F. G. Fallon et al. describe the preparation of seven 1-alkyltetrazoles by interaction of alkyl isocyanides and hydrazoic acid in benzene solution.

In the *Journal of Organic Chemistry*, Vol. 27, pp. 2085–2087 (1962) in an article entitled "The Formation of Tetrazoles by the Condensation of Organic Azides with Nitriles", W. R. Carpenter describes the preparation of various 1,5-disubstituted tetrazoles by the thermal condensation of alkyl or aryl azides with electronegative haloalkyl nitriles, e.g., trifluoromethylnitrile, perfluoropropylnitrile, none of which products was a tetrazoleacetate ester or acid.

*Angew. Chem. internat. Edit.*, Vol. 2 (1963) No. 10, on page 579 suggests that only electron-poor C≡N triple bonds of ethyl cyanoformate or of perfluoroalkyl cyanides are capable of adding organic azides to form 5-trifluoromethyl-1-alkyl-1H-tetrazoles; however, the publication does not define the conditions of reaction.

U.S. Pat. No. 3,073,731 granted Jan. 15, 1963 discloses, inter alia, the preparation of ethyl 1- and 2-tetrazoleacetates from tetrazole and ethyl bromoacetate. The products are said to be useful as plasticizers.

In *The Canadian Journal of Chemistry*, Vol. 47, (1969) pages 813–819, R. Raap et al. disclose the synthesis of several 1-, 2-, and 5-tetrazoleacetate esters by the alkylation of the triethylammonium salts of tetrazole with ethyl bromoacetate or methyl chloroacetate. This reference also discloses the hydrolysis of the esters to the acids and contains a bibliography to other related work. This reference also discloses the preparation of methyl 5-trifluoromethyl-1-tetrazolylacetate from trifluoroacetonitrile and methyl azidoacetate under the conditions given by Carpenter. [W. R. Carpenter, J. Org. Chem. 27 2085 (1962)]

b. Cephalosporin Antibiotic Patents

In U.S. Pat. No. 3,468,874 there is disclosed the preparation of some tetrazolylacetate esters by reacting, e.g., tert-butyl isocyanoacetate with hydrazoic acid or by treating a mixture of tetrazole and triethylamine in acetone with ethyl bromoacetate. The patent claims some penicillin and some cephalosporin compounds having the tetrazoleacetamido group in the 6-position of the penicillin or in the 7-position of the cephalosporin.

Netherlands Pat. No. 67/17107, published June 17, 1968 discloses the formation of 3-(substituted-tetrazolemethyl)cephalosporins by reacting a 3-azidomethylcephalosporin ester with certain dipolarophiles such as an alkoxycarbonyl cyanide.

There still exists a need to provide alternate and improved processes for preparing 1-tetrazoleacetate esters and acids and intermediates therefor which can be used for a variety of purposes, some of which are suggested by the above prior art summary. None of the prior art, to applicant's knowledge, suggests the improved, simplified process described herein or the intermediates produced therefrom.

It is an object of this invention to provide a simplified process for preparing various substituted and unsubstituted 1-tetrazoleacetate esters and acids.

It is a further object of this invention to provide novel 5-substituted-1-tetrazoleacetate esters which are readily convertible to 1H-tetrazole-1-acetic acid.

It is a specific object of this invention to provide a process for preparing 1H-tetrazole-1-acetic acid which is of interest for use in preparing penicillin and cephalosporin antibiotics such as those described in the above mentioned U.S. Pat. No. 3,468,874 as well as those described in U.S. Pat. No. 3,516,997.

SUMMARY OF THE INVENTION

This invention provides a new economical process for preparing 1H-tetrazole-1-acetate esters and acids and derivatives thereof, some of which are new compounds and are claimed hereinbelow.

I have discovered that when a mixture of an acyl cyanide and azidoacetic acid or ester thereof is heated at from about 80°C. to about 135°C. for a period of time, a 5-acyl-1H-tetrazole-1-acetate ester or acid is formed, the resultant structure being dependent upon the choice of reactants. Some of the products of this process are believed to be new and are claimed herein. Ester products described herein can be hydrolyzed to their corresponding acid by known procedures; moreover, they can be treated with a base to form appropriate alkali metal salts, such as the sodium or potassium salts. The products of the process of this invention have a variety of uses, but they are particularly of interest for use as intermediates for forming 1H-tetrazole-1-acetic acid, which is used in processes for making certain cephalosporin antibiotic compounds, such as those described in U.S. Pat. Nos. 3,468,874 and 3,516,997.

DETAILED DESCRIPTION OF THE INVENTION

The compounds of this invention have the formula

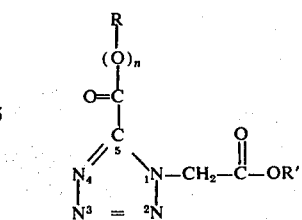

in which R' is hydrogen, an alkali metal cation, $C_1$— to $C_4$— alkyl, $C_3$— to $C_6$-cycloalkyl, phenyl, tolyl, xylyl, benzyl, p-nitrophenyl, p-nitrobenzyl, phenylethyl, 2,2,2-trichloroethyl, or phenacyl; R is $C_1$— to $C_4$-alkyl, $C_3$— to $C_6$-cycloalkyl, phenyl, naphthyl, tolyl, benzyl, p-nitrobenzyl, or an alkali metal cation, and n is zero or one; subject to the limitation that, when n is zero, R is other than an alkali metal cation.

The compounds of this invention are prepared by a process which comprises heating a mixture containing
a. a compound of the formula

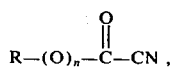

and b. a compound of the formula $$N_3—CH_2—COOR',$$

in which R, R', and n are as defined above, at a temperature of from about 80°C. to about 135°C. for a time sufficient to form the 1H-tetrazole-1-acetate ester or acid.

The compounds of this invention in which $n$ is one can be treated with aqueous acid, e.g. aqueous hydrochloric acid, to form 5-carboxy-1H-tetrazole-1-acetic acid. This structure decarboxylates to form the corresponding 1H-tetrazole-1-acetic acid.

Compounds of this invention in which $n$ is zero can be treated with aqueous acid to form the 5-acyl-1H-tetrazole-1-acetic acid compounds. These latter products can be treated with base, e.g., 1N sodium hydroxide, to form the alkali metal salt of 1H-tetrazole-1-acetic acid, which salt forms 1H-tetrazole-1-acidic acid upon acidification.

The componds of this invention in which n is one and R is other than alkali metal can be converted to the alkali metal salt, e.g., the dipotassium salt of 5-carboxy-1H-tetrazole-1-acetic acid by treatment with methanolic potassium hydroxide. These latter salts can be treated with an acid to convert them to their corresponding free acid, which decarboxylates at the 5-position to form 1H-tetrazole-1-acetic acid. The compounds of this invention in which n is zero can be treated with aqueous base to effect formation of 1H-tetrazole-1-acetic acid and an acid corresponding to that of the 5-acyl group. For example, ethyl 5-benzoyl-1H-tetrazole-1-acetate can be treated with aqueous sodium hydroxide to form sodium 1H-tetrazole-1-acetate and sodium benzoate. The sodium 1H-tetrazole-1-acetate can be converted to the acid by treatment with acid.

The acyl cyanide reactants

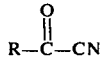

($n$ = zero) can be prepared by methods now known. They can be prepared, e.g., by reacting an acyl [R—C-(O)—] halide with a suitable metal cyanide, such as sodium cyanide or cupric cyanide. Thus, acetyl cyanide can be prepared by reacting acetyl chloride with cupric cyanide.

The cyanoformate reactant

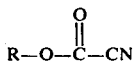

($n$ = one) can be prepared by adding concentrated aqueous ammonia to an oxalic acid mixed ester of the formula

in which R herein is as defined, in alcohol to form the oxamate, and then mixing the oxamate with a base such as pyridine, cooling and treating the mixture with trifluoroacetic anhydride to form the desired

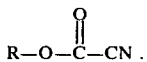

The methyl and ethyl esters of cyanoformic acid are described in the *Dictionary of Organic Compounds*, 4th Edition, Vol. 2, p. 766., edited by Ian Heilbron et al., Oxford University Press (1965). German Pat. No. 592,539, dated Feb. 17, 1934, discloses the preparation of esters of cyanoformic acid by treating esters of chloroformic acid with solid alkali cyanide containing 0.2–7.0 percent moisture at temperatures not exceeding 90°C. A procedure for preparing cyanoformate esters is suggested in *Ber.*, 70B, pp. 1012–16 (1937), by which acetoxyiminoacetyl cyanide (AcOH:CHCOCH), dropped slowly into well cooled absolute alcohol, reacts vigorously, giving, e.g., ethoxycarbonyl cyanide, b.p. 113°–115°C. at 710 mm, almost quantitatively (*C.A.*, 31, 4957[2]). The preparation of tert-butyl cyanoformate is described in *Theilheimer*, 16, 424–425 NCO, 202. Netherland Octrovia-anvrage No. 7106054, having a Datum van terinzagelegging of Nov. 8, 1971, describes the preparation of compounds such as ethoxycarbonyl cyanide.

Examples of reagents which can be used to prepare compounds of this invention include acyl cyanides and cyanoformates of the above formulas in which R is a $C_1$— to $C_4$-alkyl such as methyl, ethyl, n-propyl, isopropyl, n-butyl, isobutyl, or tert-butyl; $C_3$— to $C_6$-cycloalkyl radicals such as cyclopropyl, cyclobutyl, cyclopentyl, and cyclohexyl, and such radicals having methyl or ethyl substituents on ring carbon atoms thereof; phenyl, tolyl, xylyl, α-naphthyl, β-naphthyl, benzyl, and p-nitrobenzyl.

The azidoacetic acid or esters thereof of the formula

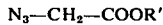

wherein R' is as defined above are useful as reactants in preparing the compounds of this invention. They can be prepared by methods now known, e.g., by displacement of a halogen atom, X, from a reactant X—CH$_2$COOR' by treatment with an alkali metal azide. For example, by reacting sodium azide with a tert-butyl haloacetate in an acetone/water mixture, the tert-butyl azidoacetate is formed, see, for example, A. T. Moore and H. N. Rydon, *Organic Syntheses*, 45, p 47 (1965). These structures can also be prepared by using the above type reactants in aqueous ethanol, see, for example, M. O. Forster and H. E. Fierz, *J. Chem. Soc.*, 93, 669 (1908). Azidoacetic acid, its ethyl ester and its acid chloride are known, being listed in the *Dictionary of Organic Compounds*, cited supra, Vol. 1, page 307.

Examples of these azidoacetic acid starting materials include azidoacetic acid itself as well as ester derivatives thereof. The esters include $C_1$— to $C_4$-alkyl esters, such as the methyl, ethyl, n-propyl, isopropyl, n-butyl, isobutyl, sec-butyl, and t-butyl esters, as well as the $C_3$- to $C_6$-cycloalkyl esters such as the cyclopropyl, cyclobutyl, cyclopentyl, cyclohexyl esters, as well as the phenyl, tolyl, xylyl, p-nitrophenyl, benzyl, p-nitrobenzyl, phenylethyl, 2,2,2-trichloroethyl, and phenacyl esters. Obviously, commercial mixtures of the acyl cyanides or cyanoformates, and azidoacetic acid or esters thereof can be used since the subsequent deesterification, decarboxylation, and purification steps will eliminate any initial structural differences.

The acyl cyanide or cyanoformate and azidoacetic acid reaction mixture can be heated neat, i.e., as a simple mixture of the two reactants, or the mixture can be dissolved or suspended in a suitable diluent or solvent for the reactants, i.e., an inert solvent that boils between 80° and 135°C., e.g., dioxane, hydrocarbons, such as toluene, xylene, and the like, or other solvents such as dimethyl sulfoxide, glacial acetic acid, pyridine, acetic anhydride, and the like.

Temperatures lower than 80°C. can be used with some pairs of reactants; however, longer times then are required. Temperatures higher than about 135°C. are not preferred due to the increased risk of spontaneous thermal reaction of some of the simpler azide reactants. A preferred temperature range for the reaction of most pairs of reactants is from about 90°C. to about 125°C.

The mixture of the reactants can be heated for any period of time necessary to produce the desired amount of 1H-tetrazole-1-acetate ester or acid product. For efficient operation of the process, reaction times may vary between about 1 and 100 hours depending upon the selected reactants, the reaction temperature, the presence or absence of diluent, and the like. Formation of the 1H-tetrazole-1-acetate from preferred reactants will generally require between about 2 to 40 hours.

When the reaction is completed, the 1H-tetrazole-1-acetate ester or acid product can be recovered from the reaction mixture by conventional means, including evaporation of excess reactants under vacuum pressure, washing of the residue with organic solvents, and crystallization of the product.

The compounds of this invention can be used as intermediates in the preparation of 1H-tetrazole-1-acetic acid which is of interest for use in making penicillin and cephalosporin antibiotics.

The 1H-tetrazole-1-acetate esters can be treated with aqueous acid or base to hydrolyze the ester group therefrom by known means and to form directly the 1H-tetrazole-1-acetic acid, which then can be used as described above. Alkali metal salts of these acids e.g., sodium, potassium, or lithium, can also be prepared by treating the ester products with methanolic or ethanolic alkali metal hydroxide.

The 5-acyl substituent in those products in which the 5-acyl group is not removed by acid hydrolysis can be removed by refluxing the 5-acyl-1H-tetrazole-1-acetate ester or acid product with a base, acidifying the mixture, extracting the 1H-tetrazole-1-acetic acid into an organic solvent, and recovering the product from the extract by evaporation.

The new compounds of the above formula are exemplified by the following:

Ethyl 5-acetyl-1H-tetrazole-1-acetate,
Ethyl 5-α-methylpropionyl-1H-tetrazole-1-acetate,
Propyl 5-p-nitrobenzoyl-1H-tetrazole-1-acetate,
tert-Butyl 5-cyclopentyloxycarbonyl-1H-tetrazole-1-acetate,
Methyl 5-cyclohexanoyl-1H-tetrazole-1-acetate,
Ethyl 5-benzoyl-1H-tetrazole-1-acetate,
Cyclopentyl 5-(p-toluyl)-1H-tetrazole-1-acetate,
p-Nitrobenzyl 5-(β-naphthoyl)-1H-tetrazole-1-acetate,
2,2,2-Trichloroethyl 5-butanoyl-1H-tetrazole-1-acetate,
Benzyl 5-propionoyl-1H-tetrazole-1-acetate,
Cyclohexyl 5-cyclopentanoyl-1H-tetrazole-1-acetate,
α-Naphthyl 5-cyclohexyloxycarbonyl-1H-tetrazole-1-acetate,
tert-Butyl 5-phenylacetyl-1H-tetrazole-1-acetate,
Phenyl 5-acetyl-1H-tetrazole-1-acetate,
Ethyl 5-ethoxycarbonyl-1H-tetrazole-1-acetate,
Methyl 5-butoxycarbonyl-1H-tetrazole-1-acetate,
Benzyl 5-phenoxycarbonyl-1H-tetrazole-1-acetate,
2,2,2-Trichloroethyl 5-(α-naphthyloxycarbonyl)-1H-tetrazole-1-acetate,
p-Tolyl 5-benzyloxycarbonyl-1H-tetrazole-1-acetate,
2,4-Xylyl 5-(p-nitrobenzyloxycarbonyl)-1H-tetrazole-1-acetate,
1-Nitrophenyl 5-(p-tolyloxycarbonyl)-1H-tetrazole-1-acetate,
Phenylethyl 5-(methoxycarbonyl)-1-H-tetrazole-1-acetate,
Phenacyl 5-(cyclopropyloxycarbonyl)-1H-tetrazole-1-acetate, and the acids, and alkali metal salts of the acids from these esters, and the like.

The invention is further exemplified by the following detailed examples illustrating the reaction of an acyl cyanide or a cyanoformate and azidoacetic acid or an ester thereof. The reactions are with and without the use of solvents, and include the hydrolysis, salt formation, and deacylation reactions.

EXAMPLE 1

1H-Tetrazole-1-acetic Acid

A mixture of ethyl azidoacetate (13.1 grams, 98.5 percent pure, 0.1 mole) and ethyl cyanoformate (20.0 grams, distilled, 0.2 mole) was heated in an oil bath at 110°–111°C. for 24 hours. Removal of excess ethyl cyanoformate in vacuo gave 22.25 grams (98% of theoretical yield) of ethyl 5-(ethoxycarbonyl)-1-H-tetrazole-1-acetate which was shown to be 91% pure by nuclear magnetic resonance.

To this reaction mixture were added 40 ml. of 1N hydrochloric acid, and the mixture was refluxed for 22 hours. The solution then was cooled, and the precipitate was filtered to give 8.4 grams of hydrated 1H-tetrazole-1-acetic acid as product. A second crop of 2.6 grams of product was obtained on further cooling of the filtrate. The precipitate (both crops) was dissolved in ethyl acetate, dried ($Na_2SO_4$), washed with ethyl acetate, and the solvent removed in vacuo to give 8.37 grams (65 percent yield, based on ethyl azidoacetate) of 1H-tetrazole-1-acetic acid, melting point 127°–129.5°C.

The analysis was as follows:
Analysis Calcd: C, 28.13; H, 3.15; N, 43.74. Found: C, 28.39; H, 3.16; N, 43.65.

Both the starting ethyl azidoacetate and the ethyl cyanoformate had been distilled. The purity of the cyanoformate was not determined; the purity of the ethyl azidoacetate was 98.5 percent as determined by gas chromatography. The yields given are based on the assumption of 100 percent pure starting materials. This reaction has been successfully repeated on pilot plant scale with less pure reactants.

EXAMPLE 2

Ethyl 5-(ethoxycarbonyl)-1H-tetrazole-1-acetate

A mixture of ethyl azidoacetate (6.4 grams, 50 millimoles) and ethyl cyanoformate (distilled, 15.0 grams, 150 millimoles) was heated on a steam bath for 40 hours. The yellow reaction mixture was concentrated under vacuum to give 9.4 grams (83 percent of theoretical yield) of an oil. Distillation of a sample at 115°–117°C. (.015 mm.) gave a viscous oil. On standing the title product, as a crystalline solid, was obtained, m.p. 26°–29.5°C. The analysis was as follows:
Analysis Calcd: C, 42.11; H, 5.30; N, 24.55 Found: C, 41.96; H, 5.14; N, 24.80

EXAMPLE 3

5-(Ethoxycarbonyl)-1H-Tetrazole-1-acetic acid

A mixture of azidoacetic acid (5.0 grams, 50 mmol.) and ethyl cyanoformate (15.0 grams, 150 millimoles,) was heated at 110°C. for 8.5 hours. The reaction mixture was cooled; crystalline product separated which was filtered and washed with toluene. The filtrate was concentrated under vacuum, and the remaining oil was cooled and seeded with a crystal of the product to give a second crop. The yield of the title product was 5.1 grams (51 percent, assuming pure starting materials), m.p. (both crops) 144°–147°C. The analysis was as follows:
Analysis Calcd: C, 36.01; H, 4.03; N, 27.99. Found: C, 36.20; H, 4.21; N, 27.77.

The reactions of Examples 1 to 3 have been carried out using a variety of reaction times, and a variety of ratios of starting materials. The reaction is favored by the use of an excess of ethyl cyanoformate and by a reaction temperature of 105°C. to 115°C. A lower temperature requires a longer reaction period but provides cleaner product.

EXAMPLE 4

Ethyl 5-Benzoyl-1H-tetrazole-1-acetate

A mixture of benzoyl cyanide (5.1 grams, 39 mmol.) and ethyl azidoacetate (5.0 grams, 39 mmol.) was heated at 105°C. for 20 hours. The solution was cooled. The crystalline product [6.5 g. (64 percent), m.p. 63°–67°C.] was separated and washed with a mixture of ethyl ether and hexane. The yield of the title product was 6.5 grams (64 percent of theoretical). The melting point was 63°–67°C. The analysis was as follows:
Analysis Calcd: C, 55.38; H, 4.65; N, 21.53. Found: C, 55.61; H, 4.74; N, 21.74.

The reactions in Examples 1 to 4 were done in the absence of solvents. The examples which follow illustrate the reaction when carried out in various solvent media.

EXAMPLE 5

Ethyl 5-(ethoxycarbonyl)-1H-tetrazole-1-acetate

A solution of ethyl azidoacetate (6.45 grams, 50 millimoles, 98.5 percent pure) and ethyl cyanoformate (10.0 grams, 100 millimoles) in 30 milliliters of dioxane was heated to reflux for 70 hours to insure complete reaction. The resulting reaction mixture was concentrated under vacuum to give 10.0 g. (88%) of the product as an oil. NMr indicated that the oil product was 88 percent pure; therefore, the actual yield from the reaction was 77 percent.

EXAMPLE 6

5-(Ethoxycarbonyl)-1H-tetrazole-1-acetic Acid

A solution of azidoacetic acid (5.0 grams, 50 millimoles) and ethyl cyanoformate (15.0 grams, 150 millimoles) in 15 ml. of toluene was heated to reflux (110°C.) for 24 hours. The reaction mixture was cooled, and the solvent was removed under vacuum. The residual solid was stirred with toluene, and the title product [4.3 g. (43%), m.p. 138°–142°C.] was separated.

The above reaction was also run in glacial acetic acid (reflux temperature, 7.5 hours, yield 36 percent, m.p. 132°–144°C.), in pyridine (reflux temperature, 18 hours, yield 17 percent as an oil); in acetic anhydride (95°C., 18 hours, yield 20 percent, m.p. 142°–146°C.); and in dioxane (reflux temperature, 24 hours, yield 45 percent, m.p. 138°–142°C.). Analysis of the product from the dioxane reaction is as follows:
Analysis Calcd: C, 36.01; H, 4.03; N, 27.99. Found: C, 36.20; H, 4.21; N, 22.77.

The following examples illustrate procedures for hydrolyzing the ester.

EXAMPLE 7

1H-Tetrazole-1-acetic Acid

A sample of ethyl 5-(ethoxycarbonyl)-1H-tetrazole-1-acetate (5.0 grams, 22 mmol.) was dripped slowly into 10 ml. of refluxing 1N hydrochloric acid. The resulting solution was allowed to continue to reflux for 30 hours. The reaction mixture was cooled, and 2.1 g. of hydrated 1H-tetrazole-1-acetic acid was isolated. This material was redissolved in ethyl acetate, dried over sodium sulfate, and the solvent was removed under vacuum. The residue was washed with a small amount of ethyl acetate and filtered. The yield of anhydrous 1H-tetrazole-1-acetic acid was 1.63 grams (58% based on the starting di-ester). The m.p. was 124°–129°C. The product analyzed as follows:
Analysis Calcd: C, 28.13; H, 3.15; N, 43.74. Found: C, 28.36; H, 3.29; N, 43.55.

EXAMPLE 8

5-(Ethoxycarbonyl)-1H-tetrazole-1-acetic acid (1.0 gram, 5 mmol.) was heated under reflux in 12 milliliters of 1N hydrochloric acid for 5 hours. After cooling, the solution was extracted with ethyl acetate (4 × 30 ml.), and the combined extracts were dried (NaSO₄) and concentrated under reduced pressure. The yield of 1H-tetrazole-1-acetic acid was 0.55 grams (86% based on the starting acid ester). The crystalline product melted at 120°–125°C. A mixture of the product with known 1H-tetrazole-1-acetic acid melted at 123°–126°C.

EXAMPLE 9

5-(Ethoxycarbonyl)-1H-tetrazole-1-acetic acid (1.0 grams, 5 mmol.) was heated under reflux in 12 ml. of 2N sodium hydroxide for 1 hour. The solution was then acidified to pH 2, and the mixture was extracted with ethyl acetate (4 × 30 ml.). The combined extracts were dried (Na₂SO₄) and concentrated under reduced pressure to give 0.2 grams (31%) of colorless crystals of 1H-tetrazole-1-acetic acid, m.p. 126°–131°C.

EXAMPLE 10

A mixture of ethyl 5-(ethoxycarbonyl)-1H-tetrazole-1-acetate (5.0 grams, 22 millimoles) and DOWEX-50W-X2 ion exchange resin (acid form, 200–400 mesh, washed with water) was heated under reflux in 10 ml. of water for 48 hours. The hot mixture was filtered, the resin was washed with 1 ml. of water, and the filtrate was concentrated to dryness. The residue was dissolved in ethyl acetate. The solution was filtered, dried ($Na_2SO_4$), and concentrated. Washing the residual cream solid with ether under vacuum gave 1.63 g. (58%) of 1H-tetrazole-1-acetic acid, m.p. 123°–129°C.

The procedure described above was repeated using 1.2 grams (5.4 mmole) of 5-(ethoxycarbonyl)-1H-tetrazole-1-acetic acid, about 0.5 grams of the ion exchange resin, and 10 ml. of water. The mixture was heated under reflux for 18 hours. The yield was 0.5 gram (72% based on the tetrazole ester) of 1H-tetrazole-1-acetic acid, m.p. 124°–127°C.

EXAMPLE 11

A sample of 5-(ethoxycarbonyl)-1H-tetrazole-1-acetic acid (6.0 grams, 30 millimoles, m.p. 134°–142°C.) was dissolved in 10 ml. of methanol. To this solution were added 15 ml. of 2N potassium hydroxide in methanol, and the mixture was heated under reflux. The resulting precipitate was filtered (3.6 grams, m.p. 202°–206°C. with dec.). Addition of an excess of a solution of potassium hydroxide in methanol to the filtrate gave a second crop (2.1 grams, m.p. 208°–227°C. with dec.). Recrystallization of the di-potassium salt of 5-carboxy-1-H-tetrazole-1-acetic acid from a mixture of methanol gave tan prisms (m.p. 245°–246°C., with dec., 57 percent yield). This product analyzed as follows after drying at 120°C.:

Analysis Calcd: C, 19.35; H, 0.81; N, 22.57; O, 25.77. Found: C, 19.26; H, 0.97; N, 22.28; O, 25.50.

A similarly prepared sample of the di-potassium salt of 5-carboxy-1H-tetrazole-1-acetic acid was hydrolyzed to 1H-tetrazole-1-acetic acid by dissolving the potassium salt in a small amount of water, acidifying the solution to pH 2 with concentrated hydrochloric acid, extracting the solution with ethyl acetate, drying the extract over sodium sulfate, removing the solvent under vacuum, treating the residual solid with a small amount of ethyl ether, and filtering. The yield of 1H-tetrazole-1-acetic acid was 40 percent of the theoretical yield based on the amount of acid mono-ester used; m.p. was 127°–128°C.

EXAMPLE 12

A sample of ethyl 5-(ethoxycarbonyl)-1H-tetrazole-1-acetate was also hydrolyzed to the 1H-tetrazole-1-acetic acid by the method described in Example 9. Amounts used were 3.0 grams of the di-ester in 5 ml. of methanol with 15 ml. of 2N potassium hydroxide in methanol. The yield was 0.87 grams of 1H-tetrazole-1-acetic acid (56 percent of theoretical yield based on the amount of the di-ester); m.p. 117°–120°C.

EXAMPLE 13

Hydrolysis of ethyl 5-benzoyl-1H-tetrazole-1-acetate to 1H-tetrazole-1-acetic acid and benzoic acid A sample of ethyl, 5-benzoyl-1H-tetrazle-1-acetate (2.0 g., 7.8 millimoles) was heated to reflux temperature in 12 ml. of 2N NaOH for 1 hour, and the solution was then acidified to pH about 2, giving a colorless precipitate which was filtered to give 1.57 g., m.p. 97°–99.5°C. which, after drying, had m.p. 122°–124°C. (lit. m.p. of benzoic acid is 123°C.)

Analysis Calcd: C, 68.85; H, 4.92. Found: C, 68.30, H, 4.80.

The acid filtrate was extracted with ethyl acetate, dried ($Na_2SO_4$), and the solvent was removed in vacuo to give 0.23 grams of colorless crystals of 1H-tetrazole-1-acetic acid, (23 percent of theoretical yield, m.p. 116°–123°C.). NMR (DMSO): δ5.4 (s,2H), 9.37 (s,1H) with 6 percent benzoic acid impurity (δ7.8, m).

I claim:

1. A compound of the formula

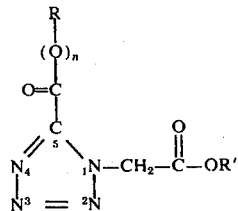

in which R' is hydrogen, an alkali metal cation, $C_1$— to $C_4$— alkyl, $C_3$— to $C_6$-cycloalkyl, phenyl, tolyl, xylyl, benzyl, p-nitrophenyl, p-nitrobenzyl, phenylethyl, 2,2,2-trichloroethyl, or phenacyl; R is $C_1$— to $C_4$-alkyl $C_3$— to $C_6$-cycloalkyl, phenyl, naphthyl, tolyl, benzyl, p-nitrobenzyl, or an alkali metal cation; and n is zero or one; subject to the limitation that, when n is zero, R is other than an alkali metal cation.

2. Compound of claim 1, in which R is $C_1$— to $C_4$— alkyl, R' is $C_1$— to $C_4$-alkyl, and $n$ is 1.

3. Compound of claim 2, in which R and R' are ethyl.

4. Compound of claim 1, in which R is $C_1$— to $C_4$-alkyl, R' is hydrogen, and $n$ is 1.

5. Compound of claim 4, in which R is ethyl.

6. Compound of claim 1, in which R is $C_1$— to $C_4$— alkyl, R' is $C_1$— to $C_4$-alkyl and $n$ is 0.

7. Compound of claim 1, in which R is $C_1$— to $C_4$— alkyl, R' is hydrogen, and $n$ is 0.

8. Compound of claim 1, in which R is phenyl, R' is $C_1$— to $C_4$-alkyl, and $n$ is 0.

9. Compound of claim 1, in which R is phenyl, R' is hydrogen, and $n$ is 0.

10. Compound of claim 1, in which R and R' each is an alkali metal cation, and n is 1.

11. Compound of claim 1, in which the alkali metal cation is potassium.

* * * * *